US009755390B2

(12) United States Patent
Hanssen et al.

(10) Patent No.: US 9,755,390 B2
(45) Date of Patent: Sep. 5, 2017

(54) PROCESS FOR MAKING BIOSENSOR

(71) Applicant: NOVIOSENSE B.V., Nijmegen (NL)

(72) Inventors: Johannes Hendrikus Leonardus Hanssen, Erlecom (NL); Christopher Wilson, Nijmegen (NL)

(73) Assignee: NOVIOSENSE B.V., Nijmegen (NL)

( * ) Notice: Subject to any disclaimer, the term of this patent is extended or adjusted under 35 U.S.C. 154(b) by 214 days.

(21) Appl. No.: 14/394,873

(22) PCT Filed: Apr. 17, 2013

(86) PCT No.: PCT/EP2013/057975
§ 371 (c)(1),
(2) Date: Oct. 16, 2014

(87) PCT Pub. No.: WO2013/156514
PCT Pub. Date: Oct. 24, 2013

(65) Prior Publication Data
US 2015/0068028 A1     Mar. 12, 2015

(30) Foreign Application Priority Data
Apr. 18, 2012   (EP) .................................. 12164644

(51) Int. Cl.
*H01R 43/033*     (2006.01)
*A61B 5/1486*     (2006.01)
(Continued)

(52) U.S. Cl.
CPC ....... *H01R 43/033* (2013.01); *A61B 5/14532* (2013.01); *A61B 5/14865* (2013.01);
(Continued)

(58) Field of Classification Search
CPC .............. A61B 5/0031; A61B 5/14532; A61B 5/14865; A61B 5/4839; A61B 2562/12;
(Continued)

(56) References Cited

U.S. PATENT DOCUMENTS 6,096,453 A * 8/2000 Grunwald ............. H01M 4/137
429/212
2003/0217463 A1   11/2003 Schmidt et al.
(Continued)

FOREIGN PATENT DOCUMENTS

DE   10 2007 038 402 A1   12/2008
DE   10 2008 049 648 A1    4/2010
(Continued)

OTHER PUBLICATIONS

Li, C et al., Toward real-time continuous brain glucose and oxygen monitoring with a smart catheter, Biosensors and Bioelectronics, Elsevier BV, NL, 2009, XP026438601, pp. 173-178.
(Continued)

*Primary Examiner* — A. Dexter Tugbang
(74) *Attorney, Agent, or Firm* — Hudak, Shunk & Farine Co., LPA

(57) ABSTRACT

A process for making a biosensor comprising a hollow coil having wires coiled in parallel and an electronic circuit component connected to the coil, the process including: 1) providing a mandrel on which wires including at least a first wire, a second wire and a third wire are wound in parallel, 2a) immersing the mandrel in a first buffer solution comprising a first bioreceptor, a first monomer and optional additives, 2b) arranging the wires such that the first wire may be used as a working electrode, the second wire may be used as a counter electrode and the third wire may be used as a reference electrode of a three electrode electrochemical cell used in an electropolymerization process, 3) passing electric current through the first wire to form a first biocompatible coating of a first polymer polymerized from the first monomer comprising the first bioreceptor on the first wire, 4) removing the coil from the mandrel, 5) connecting the wires to their respective points of the electronic circuit component such that the first wire may be used as a working
(Continued)

electrode, the second wire may be used as a counter electrode and the third wire may be used as a reference electrode and wherein the electronic circuit component is configured such that it can generate an input signal for a wireless receiver based upon the activity of the bioreceptor and wirelessly send the input signal to the wireless receiver.

20 Claims, 11 Drawing Sheets

(51) Int. Cl.
*G01N 33/543* (2006.01)
*A61N 1/05* (2006.01)
*H01R 43/28* (2006.01)
*H01M 4/1399* (2010.01)
*H01M 4/137* (2010.01)
*A61B 5/145* (2006.01)
*G01N 33/487* (2006.01)
*A61B 5/00* (2006.01)

(52) U.S. Cl.
CPC .......... *A61B 5/4839* (2013.01); *A61N 1/0563* (2013.01); *G01N 33/487* (2013.01); *G01N 33/543* (2013.01); *H01M 4/137* (2013.01); *H01M 4/1399* (2013.01); *H01R 43/28* (2013.01); *A61B 5/0031* (2013.01); *A61B 2562/12* (2013.01); *G01N 33/5438* (2013.01); *G01N 33/54306* (2013.01); *G01N 33/54393* (2013.01); *G01N 2333/904* (2013.01); *Y10T 29/49018* (2015.01); *Y10T 29/49194* (2015.01)

(58) Field of Classification Search
CPC .. A61N 1/0563; G01N 33/487; G01N 33/543; G01N 2333/904; G01N 33/54306; G01N 33/5438; G01N 33/54343; G01N 33/54393; H01R 43/033; H01R 43/28; H01M 1/137; H01M 1/1399; H01M 4/137; H01M 4/1399; Y10T 29/49018; Y10T 29/49194
See application file for complete search history.

(56) References Cited

U.S. PATENT DOCUMENTS

| 2007/0213611 | A1 | 9/2007 | Simpson et al. | |
|---|---|---|---|---|
| 2010/0137959 | A1 | 6/2010 | Seifert | |
| 2010/0317962 | A1* | 12/2010 | Jenkins | A61B 5/0422 600/411 |
| 2011/0042225 | A1* | 2/2011 | Adeloju | G01N 33/54393 205/170 |
| 2011/0072658 | A1* | 3/2011 | Dye | Y10T 29/49194 29/882 |

FOREIGN PATENT DOCUMENTS

| EP | 1 475 886 A1 | 11/2004 |
|---|---|---|
| JP | 02066431 A * | 3/1990 |
| WO | 2005 112744 A1 | 12/2005 |

OTHER PUBLICATIONS

Chunyan, Li et al, A flexible polymer tube lab-chip integrated with microsensors for smart microcatheter, Biomedical Microdevices, Kluwer Academic Publishers, vol. 10, No. 5, 2008, XP019600472, pp. 671-679.

Vedrine, C et al., Amperometric tyrosinase based biosensor using an electrogenerated polythiophene film as an entrapment support, Talanta, vol. 59, No. 3, 2003, XP055035917, pp. 535-544.

Kros, A et al., Poly(3,4-ethylenedioxythiophene)-Based Copolymers for Biosensor Applications, Journal of Polymer Science, Interscience Publishing, vol. 40, 2001, XP002361455, pp. 738-747.

Nien, Po-Chin et al., Amperometric Glucose Biosensor Based on Entrapment of Glucose Oxidase in a Poly(3,4-ethylenedioxythiophene) Film, Electroanalysis, vol. 18, No. 13-14, 2006, XP055035910, pp. 1408-1415.

Yu, B et al. Coil-Type Implantable Glucose Biosensor with Excess Enzyme Loading, Frontiers in Bioscience, vol. 10, 2005, XP009136935, pp. 512-520.

Fabiano, S et al., Poly 3,4-ethylenedioxythiophene as an entrapment support for amperometric enzyme sensor, Materials Science and Engineering, C, vol. 21, No. 1-2, 2002, XP055035906, pp. 61-67.

Vaddiraju, S et al, Emerging synergy between nanotechnology and implantable biosensors: A review, Biosensors and Bioelectrics, Elsevier BV, NL, vol. 25, No. 7, 2010, XP026905657, pp. 1553-1565.

* cited by examiner (a)

(b)

(c)

(d)

(e)

PROCESS FOR MAKING BIOSENSOR

FIELD OF THE INVENTION

The invention relates to a process for making a biosensor.

BACKGROUND OF THE INVENTION

Blood glucose monitoring is a way of testing the concentration of glucose in the blood (glycemia). It is important in the care of diabetes mellitus.

A blood glucose test is generally performed by piercing the skin (typically, on the finger tip) to draw blood, then placing the blood on a chemically active disposable strip which indicates the result either by changing colour, or changing an electrical characteristic, the latter being measured by an electronic meter.

Most people with Type 2 diabetes test at least once per day (usually before breakfast) to assess the effectiveness of their diet and exercise.

Many people with Type 2 diabetes use an oral medication to combat their insulin resistance, and test their blood glucose before and after breakfast to assess the effectiveness of their dosage. Diabetics who use insulin (all Type 1 diabetes patients and many Type 2 diabetes patients) usually test their blood sugar more often, such as 3 to 10 times per day, both to assess the effectiveness of their prior insulin dose and to help determining the time of their next insulin dose.

Improved technology for measuring blood glucose is rapidly changing the standards of care for all diabetic people. There are several methods of blood glucose testing currently available.

Chemical Test Strips: Chemical test strips are a medium cost method for monitoring blood glucose. A fairly large drop of blood, usually taken from the fingertip, is placed on a chemically prepared strip, called a blood glucose testing strip. The chemicals in the strip react with the blood, changing color according the concentration of glucose, which can then be read by comparing the color with a chart on the side of the test strip container.

Blood Glucose Meters: A blood glucose meter is an electronic device for measuring the blood glucose level. A relatively small drop of blood is placed on a disposable test strip which interfaces with a digital meter. Within several seconds, the level of blood glucose will be shown on the digital display. Sample sizes vary from 30 to 0.3 µl. Test times vary from 5 seconds to 2 minutes (modern meters are typically below 15 seconds).

Although more expensive, blood glucose meters seem a breakthrough in diabetes self care. As the drops of blood needed for the meter may be smaller, the pain associated with testing is reduced and the compliance of diabetic people to their testing regimens is improved. Although the cost of using blood glucose meters seems high; it is believed to be a cost benefit relative to the avoided medical costs of the complications of diabetes.

A recent and welcome advantage is the use of small blood drops for blood glucose testing from other places than the finger tips. This alternate site testing uses the same test strips and meter, is practically pain free, and gives the finger tips a needed break if they become sore.

A further improvement is provided by a continuous blood glucose monitor: A continuous blood glucose monitor (CGM) determines blood glucose levels on a continuous basis (every few minutes). A typical system consists of:

a) disposable glucose biosensor placed just under the skin, which is worn for a few days until replacement;
b) a link from the sensor to a non-implanted transmitter which communicates to a radio receiver;
c) an electronic receiver worn like a pager (or insulin pump) that displays blood glucose levels on a practically continuous manner, as well as monitors rising and falling trends in glycemic excursions.

Continuous blood glucose monitors measure the glucose level of interstitial fluid. Continuous monitoring allows examination of how the blood glucose level reacts to insulin, exercise, food, and other factors. The additional data can be useful for setting correct insulin dosing ratios for food intake and correction of hyperglycemia. Monitoring during periods when blood glucose levels are not typically checked (e.g. overnight) can help to identify problems in insulin dosing (such as basal levels for insulin pump users or long-acting insulin levels for patients taking injections). Monitors may also be equipped with alarms to alert patients of hyperglycemia or hypoglycemia so that a patient can take corrective action(s) (after fingerstick testing, if necessary) even in cases where they do not feel symptoms of either condition.

Studies have demonstrated that patients with continuous sensors experience less hyperglycemia and also reduce their glycosylated hemoglobin levels. This technology is an important component in the effort to develop a closed-loop system connecting real-time automatic control of an insulin pump based on immediate blood glucose data from the sensor.

SUMMARY OF THE INVENTION

It is an object of the present invention to provide a flexible process for making a biosensor.

Accordingly, the present invention provides a process for making a biosensor comprising a hollow coil comprising wires coiled in parallel and an electronic circuit component connected to the coil, the process comprising:

1) providing a mandrel on which wires including at least a first wire, a second wire and a third wire are wound in parallel, 2a) immersing the mandrel in a first buffer solution comprising a first bioreceptor, a first monomer and optional additives, 2b) arranging the wires such that the second wire may be used as a working electrode, the first wire may be used as a counter electrode and the third wire may be used as a reference electrode of a three electrode electrochemical cell used in an electropolymerisation process, 3) passing electric current through the second wire to form a first biocompatible coating of a first polymer polymerized from the first monomer comprising the first bioreceptor on the second wire, 4) removing the coil from the mandrel, 5) connecting the wires to their respective points of the electronic circuit component such that the second coil may be used as a working electrode, the first wire may be used as a counter electrode and the third wire may be used as a reference electrode and wherein the electronic circuit component is configured such that it can generate an input signal for a wireless receiver based upon the activity of the bioreceptor and wirelessly send the input signal to the wireless receiver.

It will be appreciated that in step 2b), the wires are arranged such that the second wire functions as a working electrode, the first wire functions as a counter electrode and the third wire functions as a reference electrode of a three electrode electrochemical cell used in an electropolymerisation process during step 3). Similarly, in step 5), the wires are connected to their respective points of the electronic circuit component such that the second coil functions a working electrode, the first wire functions as a counter electrode and the third wire functions as a reference electrode during the operation of the biosensor.

The coating is provided by electropolymerisation of the monomer on the surface of the selected wire. The advantage of the electropolymerisation process is that the polymer is synthesised and coated onto an electrode in a single step. This is done according to the present invention by forming a three electrode electrochemical cell used in an electropolymerisation process with the second wire used as a working electrode, the first wire used as a counter electrode and the third wire used as a reference electrode. In the electropolymerisation process, a potential is applied over the solution comprising the monomer and the bioreceptor. The potential is cycled through a specific potential range at a predetermined rate for a predetermined number of cycles. The skilled person knows the suitable conditions for enabling the electropolymerisation process for different solutions, such as the range of the potential range, rate and the number of cycles. For example, the potential range may be between 0.1 and 50 V, preferably 1 and 5 V. The rate may e.g. be between 0.001 and 50 V/s, preferably 0.1 and 5 V/s. The number of cycles may be e.g. 1 to 100, preferably 1 to 30. It is an advantage of the present invention that the electrodes used in the biosensor are used as the electrodes for the electropolymerisation process, so no extra electrodes are required in the electropolymerisation bath for the electropolymerisation process.

According to the process according to the present invention, the coating comprising the bioreceptor is provided after the wires are coiled onto the mandrel, instead of coiling wires with the coating onto the mandrel. This has an advantage that the potential damage to the coating during the winding process is avoided. A further advantage of the process according to the present invention is that the process results in a less sample dependent variation in the coating. Since many coils can be obtained by coating one long coil and cutting it thereafter into a plurality of coils each having a suitable length, the coils obtained thereby have substantially identical coating. For example, the coil on the mandrel has a length of 10-50 cm.

A further advantage of the process according to the present invention is the flexibility of the process. The mandrel with uncoated coil may be mass-produced and stored until the coating step. When the coiled wire is ready to be coated, the mandrel with the coiled wires is immersed in a suitable solution and electric current is passed through the suitable wire.

The buffer solution is preferably a phosphate buffered saline. The buffer solution for forming the biocompatible layer may comprise additives e.g. to enhance the solubility, uniformity of the coating formed and the conductive property of the solution or the coating formed. For example, a substituted dextran such as diethylaminoethyl-dextran (DEAE) has been shown to increase the stability of bioreceptors in the sensor. Examples of the additive for enhancing the conductive property include linear or cyclic aliphatic polyethers or polystyrenesulphonates. An example of surfactants includes polyethylene glycol (PEG).

The concentration of the bioreceptor in the solution depends on the type of the monomer and the bioreceptor, and may range from $1$-$10^6$ U/mL.

The polymer electropolymerised on the wire and the resin capping on the electronic circuit component are both biocompatible.

The mandrel on which the wires are coiled is made of an insulating material.

It is noted that steps 2a) and 2b) may be performed in any order. The mandrel may be immersed in the buffer solution and subsequently relevant connections to the wires may be made to form the three electrode electrochemical cell. Alternatively, relevant connections to the wires may be made to form the three electrode electrochemical cell and then the mandrel may be immersed in the buffer solution.

Preferably, the wires include a further wire and the process further comprises the steps of:

2a') immersing the mandrel in a second buffer solution comprising a second bioreceptor, a second monomer and optional additives, wherein the second bioreceptor is different from the first bioreceptor, 2b') arranging the wires such that the further wire may be used as a working electrode, the first wire may be used as a counter electrode and the third wire may be used as a reference electrode of a three electrode electrochemical cell used in an electropolymerisation process, 3') passing electric current through the further wire to form a second biocompatible coating of a second polymer polymerized from the second monomer comprising the second bioreceptor on the further wire and wherein step 5) comprises the step of connecting the further wire to the electronic circuit component such that the further wire may be used as a working electrode.

In this embodiment, different wires are selectively provided with different bioreceptors. The selective coating is provided in an easy manner by passing electric current only through selected wires. This is extremely advantageous in that more than one type of bioreceptor may be provided on the coil. By suitable combination of bioreceptors, a more accurate sensing is provided. The process of the invention may further comprise the step(s) of providing further coatings on further wires, i.e. a coil comprising three, four, five or even more wires with a bioreceptor may be provided according to the process according to the present invention.

It is again noted that steps 2a') and 2b') may be performed in any order. The mandrel may be immersed in the buffer solution and subsequently relevant connections to the wires may be made to form the three electrode electrochemical cell. Alternatively, relevant connections to the wires may be made to form the three electrode electrochemical cell and then the mandrel may be immersed in the buffer solution.

The process may further comprise the step of providing a biocompatible resin capping on the electric circuit component after step 5). The biocompatible resin capping encapsulating the electronic circuit component allows the whole unit of the biosensor to be placed inside a human body. The compactness and the flexibility of the sensor are extremely advantageous when the biosensor is to be placed in a sensitive part of the human body, such as under the eyelid. The biosensor of the present invention is hence very comfortable to wear and use.

It is noted that U.S. 2007213611 discloses in FIG. 11 a coil comprising wires coiled in parallel. The wires are used as two working electrodes and a reference electrode. This construction comprises an ex vivo end. Hence, the biosensor disclosed in U.S. 2007213611 is not to be placed inside human body.

Preferably, the wires further include a fourth wire coated with an insulating layer and step 3) comprises the step of connecting the fourth wire to the electronic circuit component such that the fourth wire may be used as an antenna. Preferably, the insulating layer is provided on the fourth wire before the fourth wire is wound on the mandrel. The wires may further include a fifth wire coated with an insulating layer which may be used as a spacer. Preferably, the insulating layer is provided on the fifth wire before the fourth wire is wound on the mandrel. The wires of the sensor according to the present invention may also include more than one of the further coiled wires which work as an antenna or a spacer. The insulating layer may e.g. be made of parylene, polytetrafluoro ethylene, fluorinated ethylene propylene, perfluroxalkoxy copolymer, polyphenylene sulfide, polyether block amide, Polyether ketone, poly amide, polyimide, polyesterimide, polyethylene such as high-density polyethylene and low-density polyethylene, polyvinylidene fluoride, or a polyurethane.

Preferably, the process according to the present invention further comprises the step of cutting the coil into a suitable length, e.g. a length of 5-50 mm, or more preferably 5 to 10 mm, between steps 4) and 5).

Preferably, the process according to the present invention further comprises the step of providing a top coating of a biocompatible material on the coil between steps 4) and 5) or on the biosensor after step 5).

The sensor obtained according to the process according to the present invention (hereinafter referred as the sensor according to the present invention) is a biosensor comprising a hollow coil comprising wires coiled in parallel and an electronic circuit component operably connected to the coil, wherein the wires include at least a first coiled wire which may be used as a counter electrode, a second coiled wire which may be used as a working electrode and a third coiled wire which may be used as a reference electrode, wherein the second coiled wire is provided with a biocompatible layer comprising a bioreceptor, wherein the electronic circuit component is capable of generating an input signal for a transceiver based upon the activity of the bioreceptor and wirelessly sending the input signal to the transceiver.

The sensor according to the present invention has a generally cylindrical shape and essentially consists of two components: a hollow coil and an electronic circuit component attached to the coil. The electronic circuit component is connected to the coiled wires at its relevant points. The electronic circuit component is preferably attached at the end of the coil. The electronic circuit component may be placed inside the coil or outside the coil. In the cases where the circuit component is placed outside the coil, the circuit component preferably extends in the axis direction of the coil so that the diameter of the sensor is not substantially increased by the circuit component protruding from the sensor in the radius direction. As used herein, the diameter of the sensor is understood as the largest dimension of the sensor perpendicular to the axis direction of the coil. Preferably, the sensor has a diameter of 0.1 to 3 mm. Preferably, the sensor has a length of 5 to 20 mm. As used herein, the length of the sensor is understood as the dimension of the total of the coil and the electronic circuit component in the axis direction of the coil. The ratio of the diameter of the coil and the length of the coil is preferably 1:1.5 to 1:200. The length of the electronic circuit component is preferably 0.1 to 5 mm.

As used herein, the term 'hollow coil' is understood to be an empty tubular body defined by one or more wires that loop around the circumference of the body, i.e. the wires are not wound around another electrode, a mandrel or other elements.

The hollow coil is advantageous in that the sensor is flexible and can follow the shape of the surrounding environment in which the sensor is placed. Hence, the biosensor does not damage the surrounding environment. The counter electrode, the working electrode and the reference electrode coiled in parallel provides a biosensor in which space is efficiently used for the same function. The compact size of the biosensor further reduces the possibility of the sensor damaging the surrounding environment.

Encapsulation of the biosensor in a biocompatible material as described above in various manners (e.g. the biocompatible resin capping on the electric circuit component, the top coating of a biocompatible material on the coil, the top coating of the biosensor) allows the whole unit of the biosensor to be placed inside a human body. This in combination with the fact that the biosensor is mechanically flexible and compact provides a biosensor which is very comfortable to wear and use. The biosensor according to the invention is therefore especially advantageous for use in a human body, especially under an eyelid.

During use, the sensor is placed in an aqueous environment containing a biomarker which interacts with the bioreceptor in the sensor. The aqueous environment may e.g. be the vascular system, the urinary tract, or other places in the body for instance intra-abdominal or intra-articular, intracapsular or intra-ocular. In particular, the sensor according to the invention can be worn under the upper or the lower eye lid in order to conveniently permit self monitoring of glucose levels in the lacrimal fluid and therewith give an indication of glucose levels in the blood. A sensor according to the invention suitable for use in this environment comprises glucose oxidase as the bioreceptor.

Glucose oxidase catalyzes the following reaction:

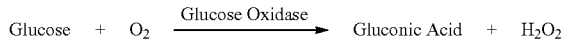

The amount of $H_2O_2$ generated is an indication of the amount of glucose in the tear liquid.

For operation of the sensor, a wireless transceiver which generates an electromagnetic field is placed close to the eye. The field powers the sensor inductively. The concentration of glucose is measured potentiometrically. The electronic circuit component generates an input signal indicating the amount of glucose present in the tear liquid and transmits the signal to the transceiver.

The electronic circuit component capable of such actions is known per se and examples of such electronic circuit component is described elsewhere in the description referring to figures. More details of examples of such electronic circuit components can be found in DE 10 2007 038 402, DE 10 2008 049 648 A1 and EP 1 475 886 B1.

The biocompatible layer prevents the bioreceptor from leaking or from being degraded by e.g. proteases present in the liquid environment.

The biocompatible layer comprises the bioreceptor, i.e. the bioreceptor is immobilized in or on the biocompatible layer by being contained in, covered by or attached to the biocompatible layer. The biocompatible layer is formed from a solution (e.g. buffer solution such as phosphate buffered saline) comprising a monomer and the bioreceptor, which is polymerized on the coil to be used as a working electrode as described above.

The materials used for forming the biocompatible layer may render the biocompatible layer electroconductive or non-electroconductive. The solution for forming the biocompatible layer may comprise additives e.g. to enhance the solubility, to enhance uniformity of the coating formed or to increase the conductive property of the solution or the coating formed. For example, a substituted dextran such as diethylaminoethyl-dextran (DEAE) has been shown to increase the stability of bioreceptors in the sensor. Examples of the additive for enhancing the conductive property include linear or cyclic aliphatic polyethers or polystyrenesulphonates. An example of surfactants includes polyethylene glycol (PEG).

The circuit component may be embedded in a biocompatible resin capping. The resin protects the circuit component from the external environment. Examples of the resin include UV curable medical adhesives such as cyano acrylates, acrylated urethanes and silicones. The other end of the coil may also be provided with the resin capping. Accordingly, in some embodiments of the invention, the electronic circuit component is attached at the end of the coil and is embedded in a biocompatible resin and the other end of the coil is provided with the biocompatible resin.

The second coiled wire is arranged to allow passing of electric current generated by the activity of the bioreceptor.

One embodiment in which this is achieved is a sensor according to the invention wherein the second coiled wire has a Pt surface. This is advantageous in that a wide choice of materials is allowed for the coatings provided thereon. $H_2O_2$ decomposes into water and oxygen on the platinum working electrode. The electrochemical decomposition is measured potentiometrically.

A further embodiment in which this is achieved is a sensor according to the invention wherein the biocompatible layer comprising the bioreceptor is electroconductive. The electrons generated by the decomposition of $H_2O_2$ are passed to the second coiled wire via the electroconductive layer in which the bioreceptor is present. In this case, the second coiled wire may be any electrode material for example those having a surface of Pt, Pd or an alloy thereof.

The surface of the coiled wires may be made of a different material from the inside of the wires or the same material may be used for the surface and the inside of the coiled wires. For example, the coiled wires may be made of stainless steel on which other metals such as Pt, Pd and Ag are coated.

Preferably, the coil is encapsulated in a top layer of a biocompatible material. The top layer encloses the coil when the coil is placed in a wet environment. This additional layer further increases the suitability of the use of the biosensor in a sensitive human body such as under the eyelid In preferred embodiments, the biocompatible layer comprising the bioreceptor is electroconductive and the coil is encapsulated in a top layer of a biocompatible material.

The following specific embodiments of the sensor according to the present invention are mentioned:

the second coiled wire has a Pt surface, the biocompatible layer comprising the bioreceptor is electroconductive and the coil is encapsulated in a top layer of a biocompatible material;

the second coiled wire has a Pt surface, the biocompatible layer comprising the bioreceptor is electroconductive and the coil is not encapsulated in a top layer of a biocompatible material;

the second coiled wire has a Pt surface, the biocompatible layer comprising the bioreceptor is not electroconductive and the coil is encapsulated in a top layer of a biocompatible material;

the second coiled wire has a Pt surface, the biocompatible layer comprising the bioreceptor is not electroconductive and the coil is not encapsulated in a top layer of a biocompatible material;

the second coiled wire has a surface made of a non-Pt metal, the biocompatible layer comprising the bioreceptor is electroconductive and the coil is encapsulated in a top layer of a biocompatible material and the second coiled wire has a surface made of a non-Pt metal, the biocompatible layer comprising the bioreceptor is electroconductive and the coil is not encapsulated in a top layer of a biocompatible material.

According to the present invention, only the coil may be encapsulated in the top layer or the sensor (the coil and the electronic circuit component) may be encapsulated in the top layer.

The biocompatible material used for the top layer may be any known suitable material, as long as it is permeable to the biomarker that interacts with the bioreceptor in the sensor according to the present invention.

Preferably, the biocompatible material of the top layer is a hydrophilic material. Preferably, the biocompatible material is a biocompatible hydrogel.

In some embodiments, the hydrogel is preferably a copolymer of a hydrophobic reactive monomer and a hydrophilic reactive monomer. Suitable examples may be the following combinations of hydrophilic and hydrophobic monomeric building blocks: (i) hydrophilic: N-vinylpyrrolidinone, hydrophobic: n-butylmetha-crylate; (ii), hydrophilic: hydroxyethylmethacrylate, hydrophobic: methylmethacrylate; (iii), hydrophilic: N-dimethylaminoethylmethacrylate, hydrophobic: cyclohexylacrylate.

In some embodiments, the hydrogel is a polysaccharide, for example those based on hyularon or chitosan and those based on synthetic polysaccharides such as cellulose ethylsulphonate or carboxymethylcellulose or mixtures thereof.

In some embodiments, the hydrogel is a block copolymer of polyethers differing by at least one carbon in the aliphatic region e.g. an ABA block co-polymer of polyethylene glycol and polypropylene glycol.

In some embodiments, the hydrogel is nafion (tetrafluoroethylene-perfluoro-3,6-dioxa-4-methyl-7-octenesulfonic acid copolymer).

The electroconductive polymer in the biocompatible layer comprising the bioreceptor is preferably a polymer synthesised from an optionally substituted five-membered heterocycle of formula (I)

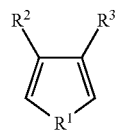

(I)

wherein $R^1$ stands for a hetero atom, preferably N, S or O, wherein $R^2$, $R^3$ are each independently selected from the group of H, optionally substituted alkyl of preferably 1 to 4 C atoms, wherein the alkyl may be substituted with for example a hydroxyl group, alkyl group and alkyl ether, optionally substituted o-alkyl, and wherein $R^2$ and $R^3$ may form a ring together with the carbon atoms to which they are connected.

Examples of substituted 5 membered heterocycles where the hetero atom is sulphur is 3,4-alkylenedioxythiophene.

Preferred examples of 3,4-alkylenedioxythiophene include
2,3-dihydrothieno[3,4-b][1,4]dioxine
3,4-dihydro-2H-thieno[3,4-b][1,4]dioxepine
or 2,3,4,5-tetrahydrothieno[3,4-b][1,4]dioxocine. Other preferred examples of 3,4-alkylenedioxythiophene include
2,3-disubstituted-2,3-dihydrothieno[3,4-b][1,4]dioxine
2-substituted-2,3-dihydrothieno[3,4-b][1,4]dioxine
3-substituted-3,4-dihydro-2H-thieno[3,4-b][1,4]dioxepine
3,3-disubstituted-3,4-dihydro-2H-thieno[3,4-b][1,4]dioxepine
3,3-bis(substituted)-3,4-dihydro-2H-thieno[3,4-b][1,4]dioxepine
or a 2,3,4,5-tetrasubstituted-2,3,4,5-tetrahydrothieno[3,4-b][1,4]dioxocine
Particularly preferred are
2,3-dimethyl-2,3-dihydrothieno[3,4-b][1,4]dioxine
3,3-dimethyl-3,4-dihydro-2H-thieno[3,4-b][1,4]dioxepine
3,3-bis(methoxymethyl)-3,4-dihydro-2H-thieno[3,4-b][1,4]dioxepine
2,3,4,5-tetramethyl-2,3,4,5-tetrahydrothieno[3,4-b][1,4]dioxocine
2,3-dihydrothieno[3,4-b][1,4]dioxin-2-ol
2-methyl-2,3-dihydrothieno[3,4-b][1,4]dioxine
2,3-dihydrothieno[3,4-b][1,4]dioxin-2-ylmethanol
2-phenyl-2,3-dihydrothieno[3,4-b][1,4]dioxine
Sodium 4-(2,3-dihydrothieno[3,4-b][1,4]dioxin-2-ylmethoxy)butane-1-sulfonate
3-methyl-3,4-dihydro-2H-thieno[3,4-b][1,4]dioxepine
3,4-dihydro-2H-thieno[3,4-b][1,4]dioxepin-3-ylmethanol
3,4-dihydro-2H-thieno[3,4-b][1,4]dioxepin-3-ol
5,10-dihydrothieno[3,4-c][2,5]benzodioxocine
or 2-methyl-2,3-dihydrothieno[3,4-b][1,4]dioxine. Most preferred monomer is the unsubstituted 3,4-ethylenedioxythiophene.

Examples of non-electroconductive material used for the biocompatible layer comprising the bioreceptor include 3,4-dihydroxy-L-phenylalanine (L-DOPA), chitosan, Nafion (tetrafluoroethylene-perfluoro-3,6-dioxa-4-methyl-7-octenesulfonic acid copolymer).

Preferably, the third coiled wire is a silver/silver chloride reference electrode. The reference electrode may also function as an antenna by being connected to the relevant points of the electronic circuit component.

The parallel wires of the sensor according to the present invention may further include a fourth coiled wire comprising an insulating layer which may be used as an antenna and/or a fifth coiled wire comprising an insulating layer which may be used as a spacer. The wires of the sensor according to the present invention may also include more than one of the further coiled wires which work as an antenna or a spacer. The insulating layer may e.g. be made of parylene, polytetrafluoro ethylene, fluorinated ethylene propylene, perfluroxalkoxy copolymer, polyphenylene sulfide, polyether block amide, Polyether ketone, poly amide, polyimide, polyesterimide, polyethylene such as high-density polyethylene and low-density polyethylene, polyvinylidene fluoride, or a polyurethane.

The parallel wires of the sensor according to the present invention may include a further coiled wire provided with a biocompatible layer comprising a bioreceptor, which may be used as a further working electrode. The further coiled wire may have the same construction as the second coiled wire. The further coiled wire may also have a different construction from the second coiled wire, as long as it can work as a working electrode by suitable connection to the electronic circuit component. In particular, the bioreceptors on different working electrodes may be different. The coil of the sensor according to the present invention may also comprise more than one further coiled wire which work as a further working electrode.

The bioreceptor in the sensor according to the present invention is preferably an oxidoreductase, i.e. a redox enzyme. Preferably, the bioreceptor is an oxidoreductase of the enzyme commission groups EC 1.X.3 where X=1-17. Examples of the oxidoreductase of this type include EC1.1.3 (e.g. Glucose oxidase, L-gulonolactone oxidase, Thiamine oxidase, Xanthine oxidase), EC 1.3.3 (e.g. Protoporphyrinogen oxidase), EC 1.4.3 (e.g. Monoamine oxidase), EC 1.5.3 (e.g. Sarcosine oxidase, Dihydrobenzophenanthridine oxidase), EC 1.7.3 (e.g. Urate oxidase), EC 1.8.3 (e.g. Sulfite oxidase), EC 1.9.3 (e.g. Cytochrome c oxidase), EC 1.10.3 (e.g. Catechol oxidase, Laccase) and EC 1.16.3 (e.g. Ceruloplasmin).

The bioreceptor may preferably be chosen from the group consisting of glucose oxidase, lactate dehydrogenase, pyruvate dehydrogenase and pyruvate oxidase.

BRIEF DESCRIPTION OF THE DRAWINGS

The invention will be described in detail below referring to the drawings in which.

DETAILED DESCRIPTION OF THE INVENTION

Figure 1:
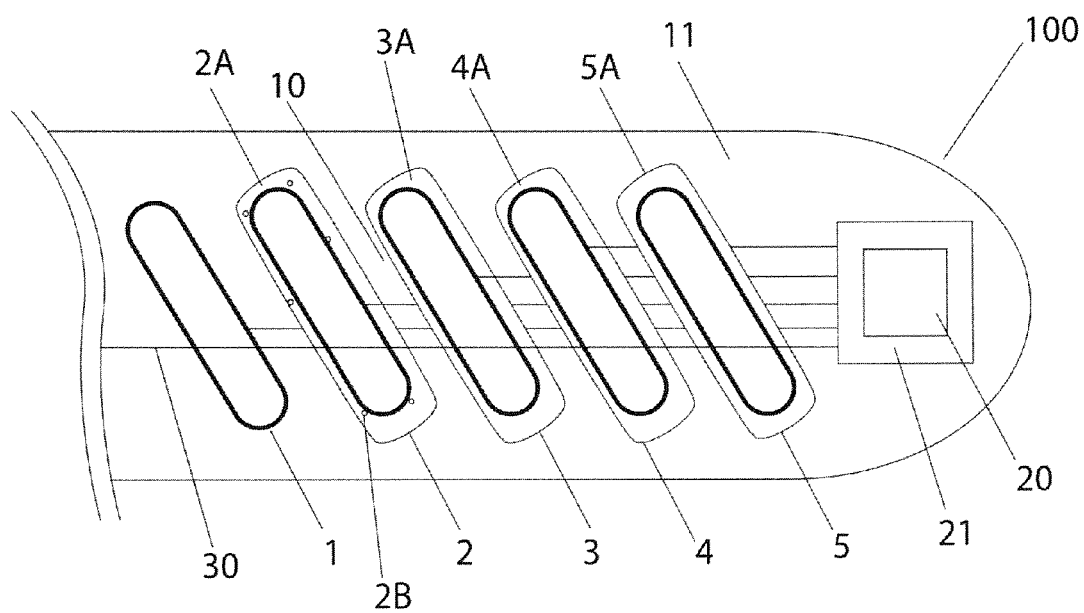
FIG. 1 schematically illustrates an embodiment of the sensor according to the invention.

FIG. 1 illustrates an embodiment of the sensor 100 according to the present invention. The sensor 100 comprises a hollow coil 10 comprising a first coiled wire 1, a second coiled wire 2, a third coiled wire 3, a fourth coiled wire 4 and a fifth coiled wire 5 coiled in parallel. The hollow coil 10 is connected to an electronic circuit 20. The electronic circuit 20 is attached at the end of the coil 10. The hollow coil 10 in this example has a diameter of 1 mm.

The first coiled wire 1 functions as a counter electrode. The second coiled wire 2 functions as a working electrode. The third coiled wire 3 functions as a reference electrode. The fourth coiled wire 4 functions as an antenna. The fifth coiled wire 5 functions as a spacer.

The hollow coil 10 and the electronic circuit 20 are covered in a continuous top layer 11. The electronic circuit 20 is embedded in a resin layer 21 under the top layer 11.

The first coiled wire 1 is made of a platinum-plated stainless steel and is provided only with the top layer 11.

The second coiled wire 2 is made of a platinum-plated stainless steel and is provided with a polymer layer 2A under the top layer 11. The polymer layer 2A is electron conductive and comprises a bioreceptor 2B, glucose oxidase in this example.

The third coiled wire 3 is a silver plated stainless steel and is coated with a silver chloride layer 3A under the top layer 11.

The fourth coiled wire 4 is made of a stainless steel and is coated with an insulating layer 4A under the top layer 11. The insulating layer 4A is made of e.g. PTFE.

The fifth coiled wire 5 is made of a stainless steel and is coated with an insulating layer 5A under the top layer 11. The insulating layer 5A is made of e.g. PTFE.

A return wire 22 for the antenna 4 extends from the electronic circuit component 2 to a different loop (not shown) of the fourth coiled wire 4, so that a closed loop antenna is formed.

During use, the sensor of this embodiment is placed in the lower eyelid filled with a tear fluid. Glucose in the tear liquid produces $H_2O_2$ by the catalytic function of glucose oxidase in the polymer layer 2A of the second coiled wire 2.

The sensor operates by an electromagnetic field generated by a transceiver (not shown) placed close to the lower eyelid. The electromagnetic field induces an electric current through the coil. The level of the electric current depends on the level of $H_2O_2$ which in turn depends on the level of glucose in the tear liquid. The electronic circuit 20 generates a signal indicating the level of glucose and sends it to the external device through coil 4.

Figure 2:
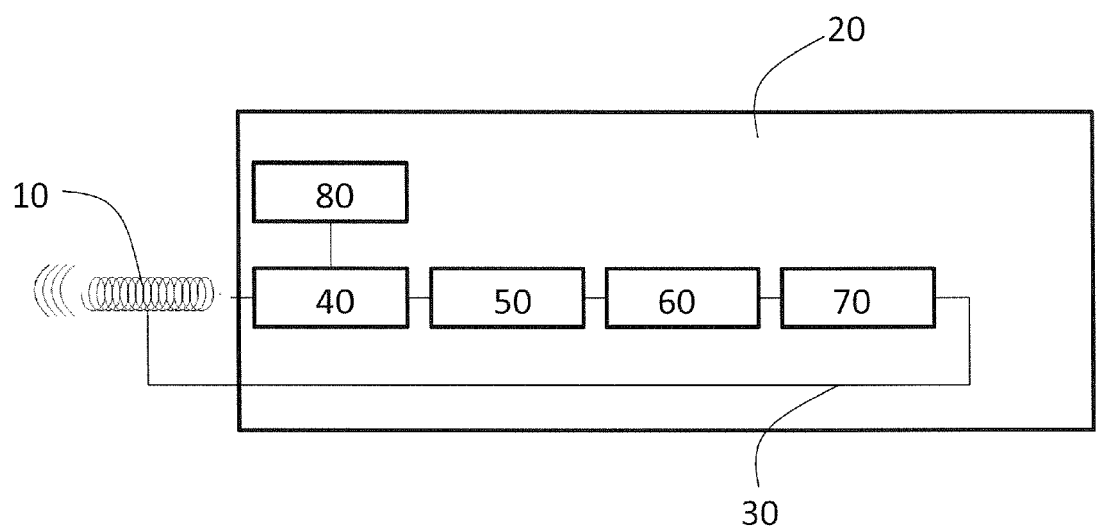
FIG. 2 is a schematic diagram of an embodiment of the sensor according to the invention in which the details of the electronic circuit component are shown.

FIG. 2 schematically illustrates an embodiment of the sensor according to the invention. The electronic circuit 20 component is illustrated more in detail. In this example, the coil 10 comprises a coiled wire used as an antenna. The electronic circuit component 20 consists of a potentiostat 40, a reference source 80, an A/D converter 50, a microprocessor 60 and a RF transceiver 70. The potentiostat 40 translates the current of the working electrode into a voltage. This voltage is digitized by the A/D converter 50 into counts. The reference source 80 provides necessary bias voltages to the potentiostat 40. The microprocessor 60 controls the processing of the sensor. The counts, i.e. the sensor raw data, are converted into a transmit data packet, for example as described in the Norm ISO 18000-3, by the microprocessor 60. The RF transceiver 70 is wirelessly connected to a reader unit (not shown here) using inductive coupling. The RF transceiver 70 is connected to the antenna coil by a return wire 30. The RF transceiver 70 transmits the data packet containing the sensor raw data to the reader unit using the antenna coil. The sensor is wirelessly powered also using inductive coupling. For data and power transmission the same antenna coil is used.

Figure 3:
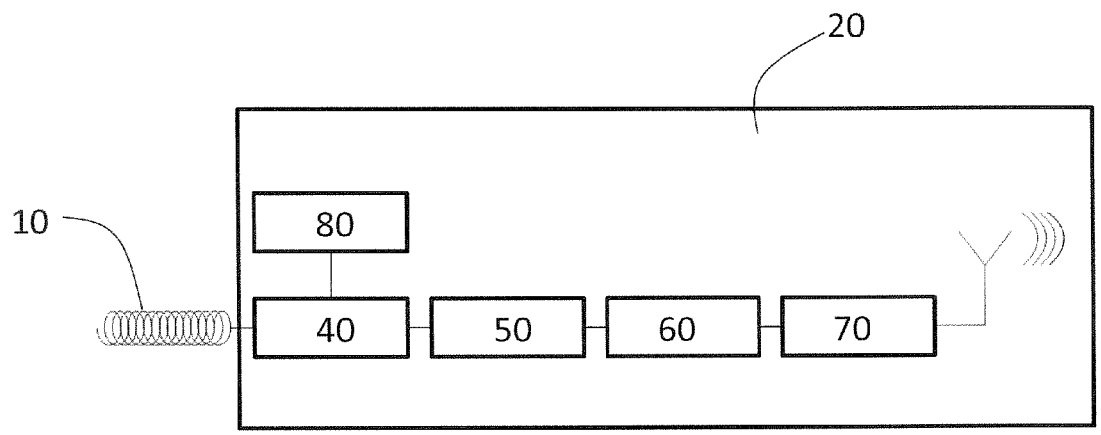
FIG. 3 is a schematic diagram of a further embodiment of the sensor according to the invention in which the details of the electronic circuit component are shown.

FIG. 3 schematically illustrates an embodiment of the electronic circuit component of the sensor according to the invention. FIG. 3 is identical to FIG. 2 except for that the antenna. In this example, the coil does not comprise a coiled wire used as an antenna. Instead, the electronic circuit component comprises an antenna for the data and power transmission.

Figure 4:
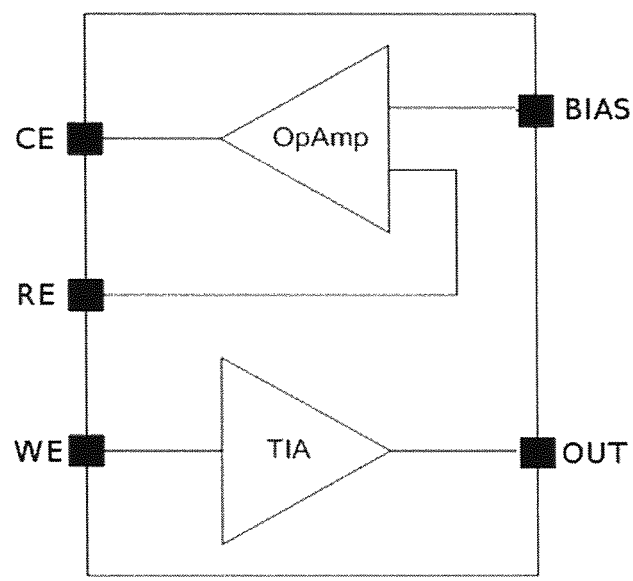
FIG. 4 illustrates the working principle of the potentiostat in the electronic circuit component in the sensor according to the present invention.

FIG. 4 illustrates the working principle of the potentiostat in the electronic circuit component in the sensor according to the present invention. The potentiostat consists of a differential input amplifier (OpAmp) and a transimpedance amplifier (TIA). The differential input amplifier compares the potential between the working (WE) and reference (RE) electrodes to adjust the required working bias potential. For this purpose, the voltage between the working and the reference electrodes may be amplified and applied to the counter electrode as an error signal. Thus the voltage between working and reference electrodes is maintained to be constant. The transimpedance amplifier is connected to the working electrode and converts the cell current into a voltage (Out). The transimpedance amplifier keeps the potential of the working electrode at virtual ground.

FIGS. 5-8 illustrate various examples of the configuration of the biosensor according to the present invention.

Figure 5:
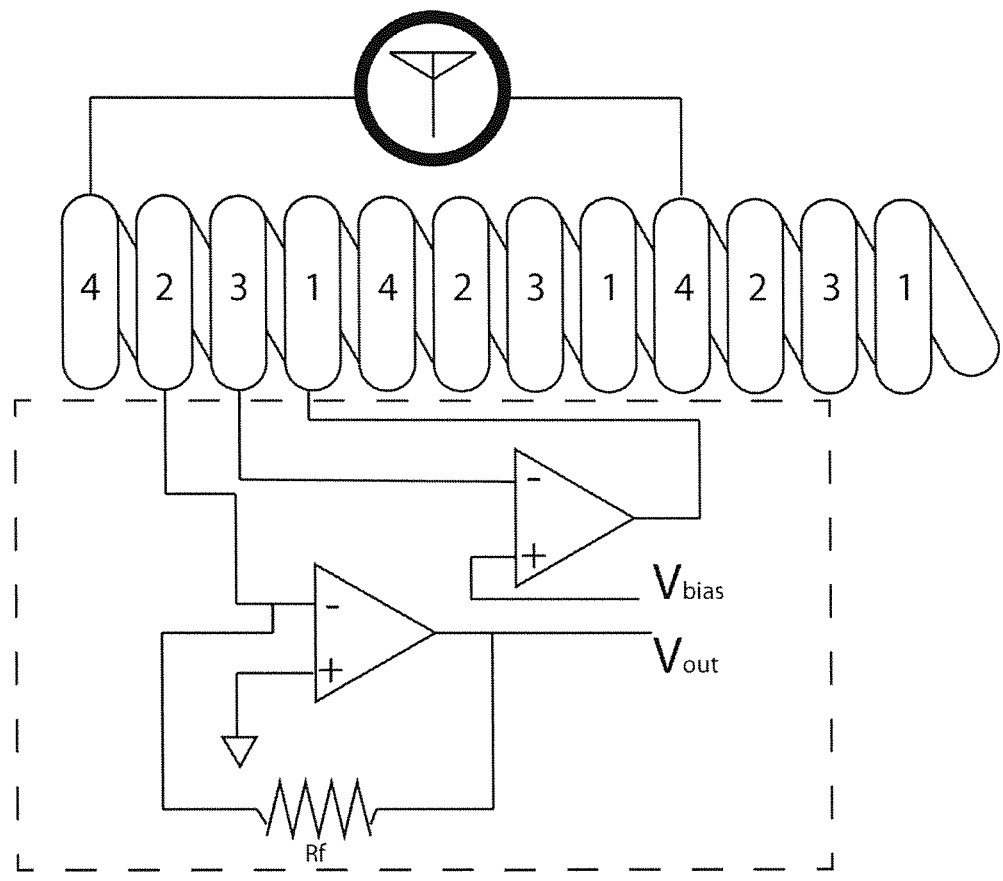
FIGS. 5-8 illustrate various examples of the configuration of the biosensor according to the present invention.

In FIG. 5, the coil consists of four wires coiled in parallel. The wires are connected to the respective points of the electronic circuit component so that they respectively function as: counter electrode 1, working electrode 2, reference electrode 3 and antenna 4.

Figure 6:
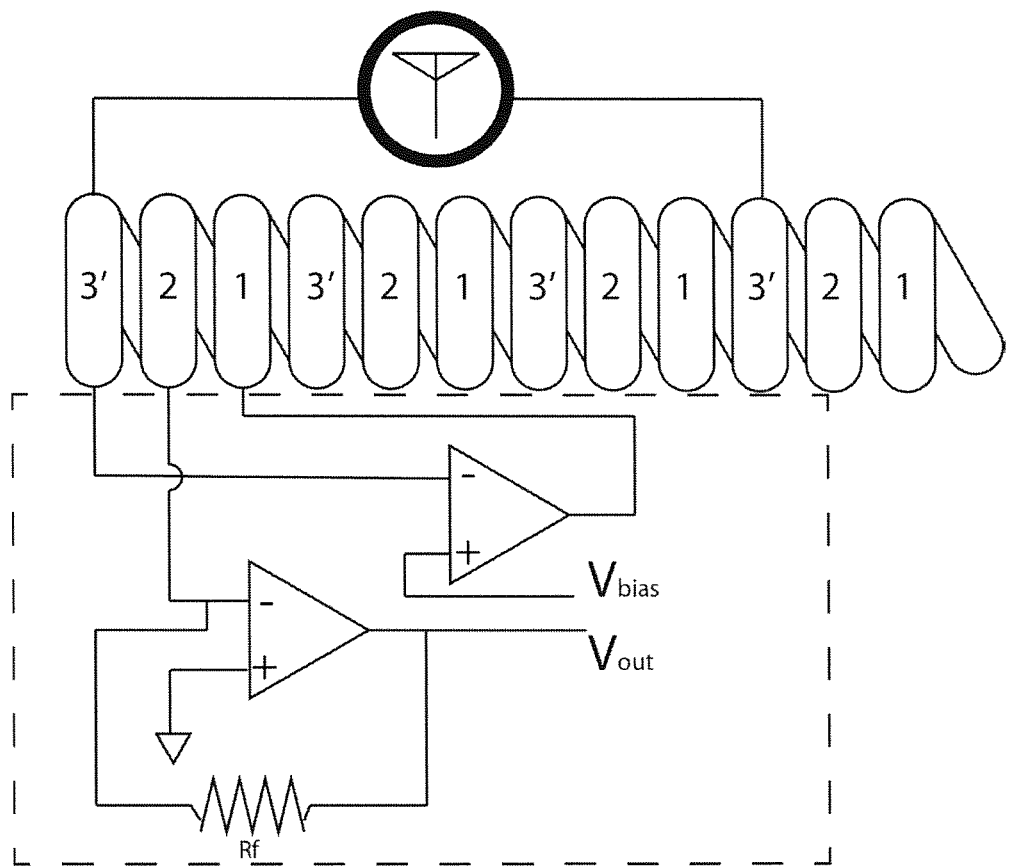

In FIG. 6, the coil consists of three wires coiled in parallel. The wires are connected to the respective points of the electronic circuit component so that they respectively function as: counter electrode 1, working electrode 2, reference electrode 3'. In this embodiment, the wire which functions as a reference electrode also functions as an antenna.

Figure 7:
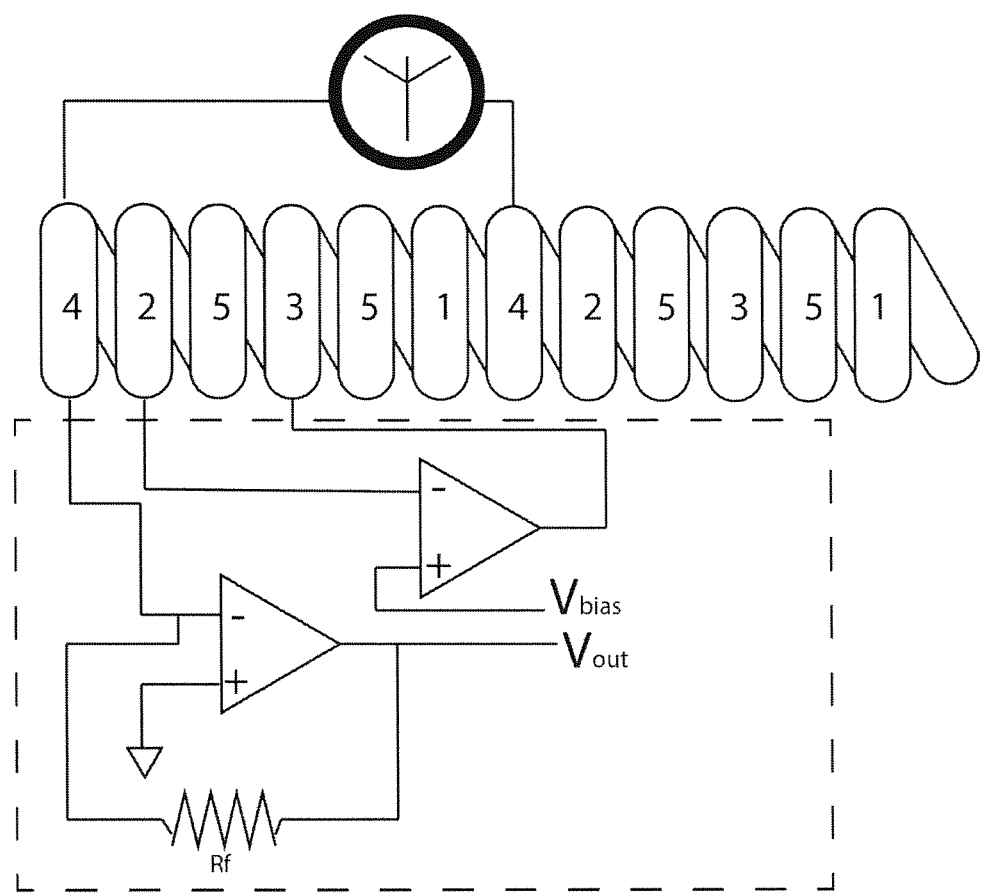

In FIG. 7, the coil consists of five wires coiled in parallel. The wires are connected to the respective points of the electronic circuit component so that they respectively function as: counter electrode 1, working electrode 2, reference electrode 3, antenna 4 and spacer 5.

Figure 8:
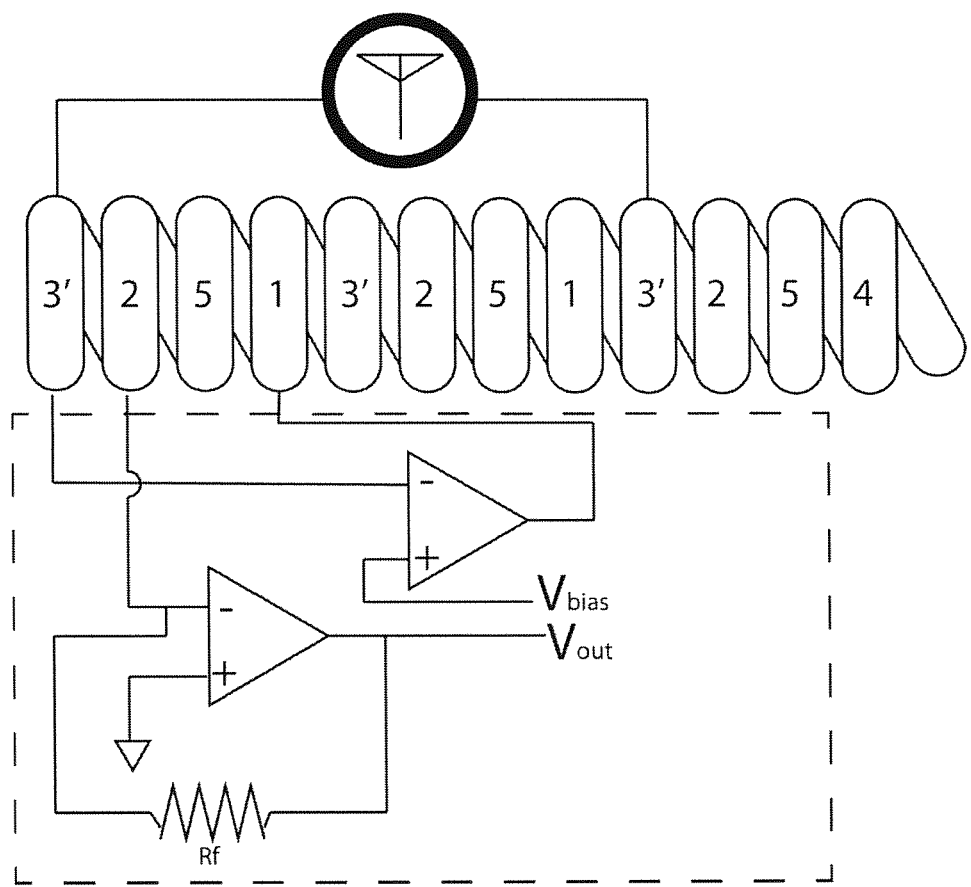

In FIG. 8, the coil consists of four wires coiled in parallel. The wires are connected to the respective points of the electronic circuit component so that they respectively function as: counter electrode 1, working electrode 2, reference electrode 3' and spacer 5. In this embodiment, the wire which functions as a reference electrode 3' also functions as an antenna.

Figure 9:
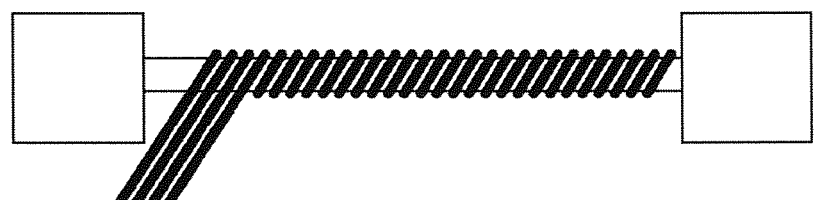
FIG. 9 illustrates an example of the process according to the invention.
Figure 9:
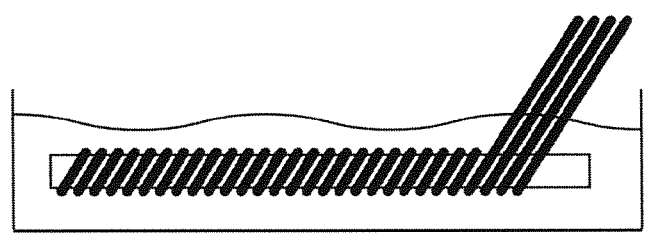
Figure 9:
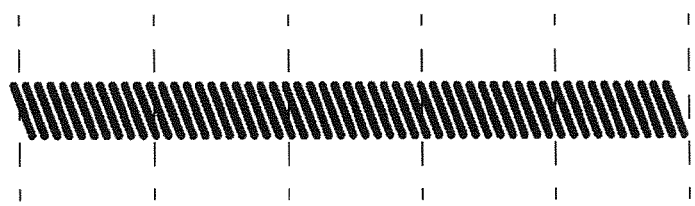
Figure 9:
Figure 9:

An example of the process according to the invention is described referring to FIG. 9.

Four wires are wound on a mandrel in parallel, as shown in FIG. 9(*a*). In this example, three wires are made of a platinum-plated stainless steel and are uncoated. The remaining one wire is a silver plated stainless steel and is coated with a silver chloride layer.

Subsequently, the mandrel with the coiled wires are placed in a phosphate buffered saline (PBS) of EDOT, glucose oxidase and PEG as shown in FIG. 9(*b*). Two platinum-lated stainless steel wire and one Ag/AgCl wire are connected to an external electronic circuit so that a three electrode electrochemical cell capable of an electropolymerisation process is formed. Electric current is passed through the uncoated platinum-plated stainless steel wire acting as the working electrode. For example, the potential is cycled from 0.3V between 0.2-1.2 V at a scan rate of 0.1 V/s for 30 cycles. EDOT polymerizes at the surface of the wire and forms a coating thereon of PEDOT comprising glucose oxidase. A coil in which only one of the wires is coated with PEDOT comprising glucose oxidase is thus obtained.

The mandrel is taken out of the solution and the excess solution is removed by wiping. The mandrel is then placed in a second buffer solution of EDOT, lactate dehydrogenase and additives. Again, a three electrode electrochemical cell capable of an electropolymerisation process is formed, but using the remaining uncoated Pt wire as the working electrode. Electric current is passed through the working electrode. EDOT polymerizes at the surface of the wire and forms a coating thereon of PEDOT comprising lactate dehydrogenase.

A coil in which one of the wires is coated with PEDOT comprising glucose oxidase and another one of the wires is coated with PEDOT comprising lactate dehydrogenase is thus obtained. The mandrel is taken out of the solution and the excess solution is removed by wiping. The coil of four wires is removed from the mandrel.

The coil is subsequently cut into a number of coils having a suitable length, e.g. 1 cm, as shown in FIG. 9(c). The four wires of the coil of the suitable length are connected to an electric circuit component such that they function as follows:

The wire coated with PEDOT comprising glucose oxidase and the wire coated with PEDOT comprising lactate dehydrogenase: working electrode The uncoated wire: counter electrode The silver plated stainless steel with a silver chloride layer: reference electrode After the connections are made, the electronic circuit component is encapsulated with a biocompatible resin. The other side of the coil is also provided with an end capping of the biocompatible resin. The result is shown in FIG. 9(d).

The assembly of the coil and the electronic circuit component is coated with a polysaccharide. A sensor encapsulated in a polysaccharide hydrogel is thus obtained.

EXAMPLES

Example 1: Preparation of a Pt Working Electrode with an Electroconductive Layer of PEDOT, Without a Top Layer (Non-Parallel Wires)

An (enzyme) working electrode was prepared by dispersing 3,4-ethylenedioxythiophene (EDOT) (~$10^{-2}$ M) in phosphate buffered saline (PBS), GOX (~110 U/mL) was added and was allowed to dissolve without agitation.

A three electrode electrochemical system was used whereby a platinum coiled wire (0.01 mm diameter) functions as the working electrode (WE), a platinum coiled wire functions as the counter electrode (CE) and a coiled Ag/AgCl/saturated KCl functions as the reference electrode (RE). The wires were not coiled in parallel, but existed as separate components. The electrodes formed an electrochemical cell for an electropolymerisation process.

The WE was ultrasonically cleaned in ultra-pure water before use. The electrodes were placed in the EDOT/GOx/PBS solution and the potential was cycled between 0.2 and 1.2V/s for 15 cycles. The resulting coated electrode was washed with fresh PBS solution and could be used directly resulting in an immobilized GOx PEDOT matrix onto the platinum wire (Pt/PEDOT/GOx).

Example 2: Sensing Function

A glucose calibration curve was made using the three electrode setup obtained by Example 1.

Glucose PBS solutions from 0.00 to 0.40 mM with steps of 0.05 mM and from 0.50 to 8.00 mM with steps of 0.5 mM were prepared.

Amperometry was performed for the different solutions. One potential step of 600 mV vs Ag/AgCl/saturated KCl was applied and the current was measured for 600 s, while the solution was stirred continuously. The average current and the standard deviation between 60 and 600 seconds was calculated and plotted against the glucose concentration.

Figure 10:
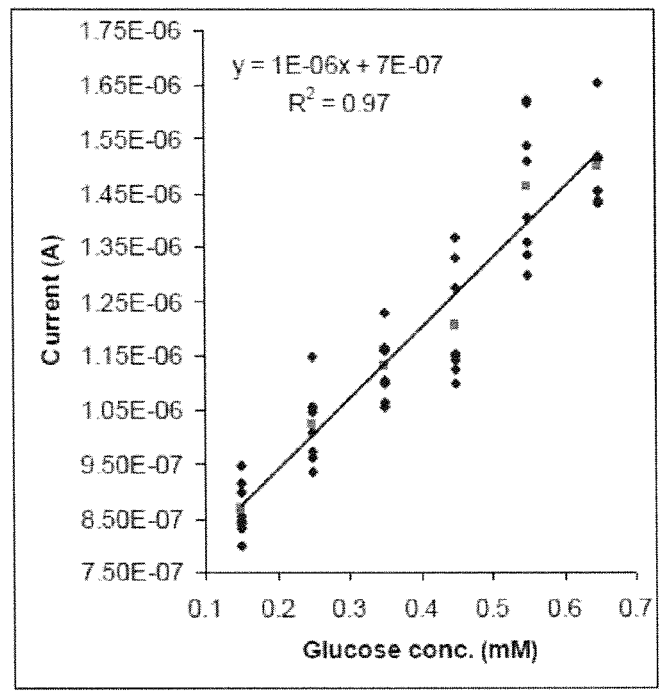
FIGS. 10-13 show various graphs obtained by experiments relating to the invention.
Figure 11:
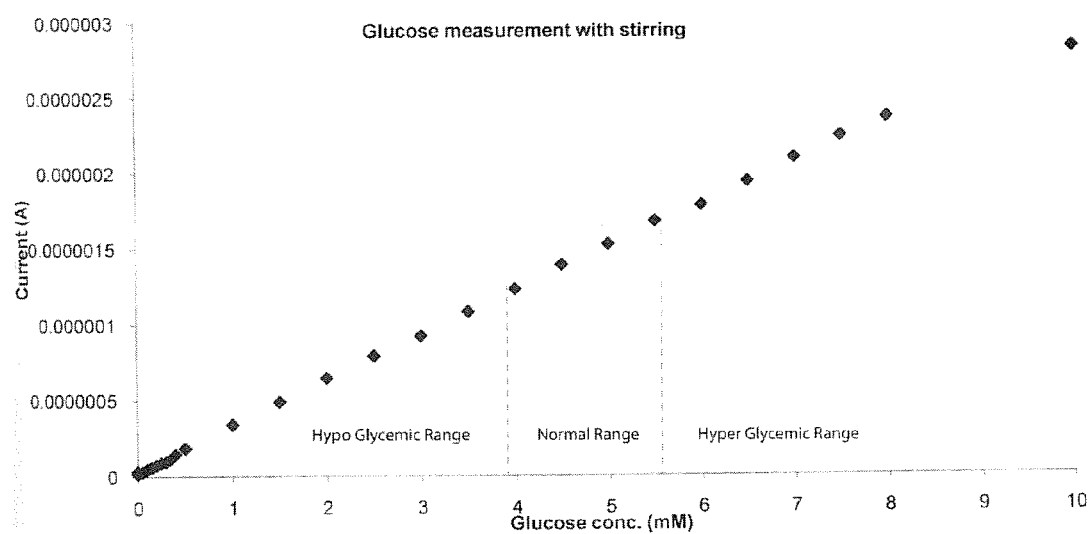

It was observed that the current was linearly proportional to the glucose concentration in a range between 0 and 10 mM. The calibration curve produced for the low concentration range (0 to 0.7 mM) is shown in FIG. 10. Symbols represent individual measurement points and the straight line represents the least squares fit to these points. Additional examples demonstrating the detection of glucose at hyperglycemic, physiological and hypoglycemic concentrations are shown in FIG. 11. The region between 0 mM and 3.9 mM represents the hypoglycemic region, the region between 3.9 mM and 5.5 mM represents the normal glucose region and the region above 5.5 mM represents the hyperglycemic region.

Example 3: Preparation of a Pt Working Electrode with an Electroconductive Layer of PEDOT Without a Top Layer (Non-Parallel Wires)

An (enzyme) working electrode was prepared by, dispersing 3,4-ethylenedioxythiophene (EDOT) (0.01M) in phosphate buffered saline (PBS) containing PEG8000 (0.001M). To the EDOT solution was added GOx (5312.7 U) which was allowed to dissolve without agitation.

A three-electrode electrochemical system was used: consisting of coiled working electrode (WE), diameter 1.5 mm, a coiled platinum wire as counter electrode (CE) and a Ag/AgCl/saturated KCl reference electrode (RE). The electrodes formed an electrochemical cell for an electropolymerisation process.

The WE was precleaned by sequential washing in $H_2SO_4$, ultrapure water and finally in PBS. The electrodes were placed in the EDOT/GOx/PEG/PBS solution and the potential was cycled from 0.3V between 0.2-1.2 V at a scan rate of 0.1 V/s for 30 cycles.

A coiled platinum wire coated with a conductive coating of PEDOT comprising GOx was thus obtained.

Example 4: Sensing Function

Figure 12:
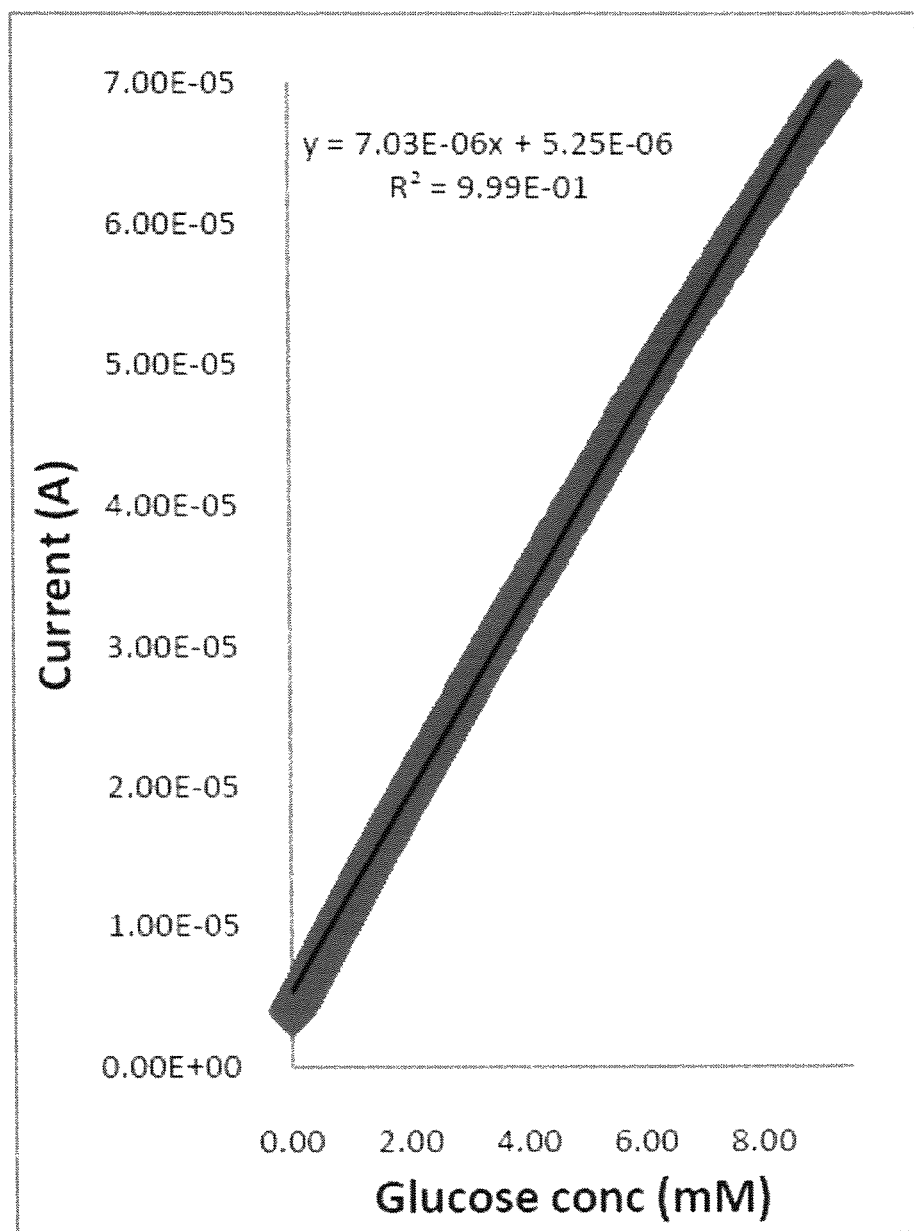

Example 2 was repeated, but the working electrode was replaced by the electrode obtained by example 3. Calibration curves were produced showing that the measured current through the working electrode was substantially proportional to the glucose concentration, as shown in FIG. 12.

Example 5: Parallel Wires

Examples 1-4 are repeated, except that the wires used as the WE, CE and RE are coiled in parallel. No substantial difference is noted in the sensing behavior between the examples wherein the wires not coiled in parallel are used (Examples 1-4) and the examples wherein the wires coiled in parallel are used (Example 5).

Example 6: Parallel Wires with a Top Layer

Examples 1-4 are repeated, except that the wires used as the WE, CE and RE are coiled in parallel and the coil is dip coated with a solution of Nafion (tetrafluoroethylene-perfluoro-3,6-dioxa-4-methyl-7-octenesulfonic acid copolymer) (10 wt % in water) and allowed to dry at room temperature. A coil encapsulated in Nafion is obtained. No substantial difference is noted in the sensing behavior between Examples 5 and 6.

Example 7: Preparation of a Pt Working Electrode with an Electroconductive Layer of PEDOT (Parallel Wires)

A wire of platinum plated stainless steel, diameter 0.152 mm, may be coated with a copolymer of BMA and NVP. Another wire of platinum plated stainless steel, diameter 0.152 mm, may be coated electrochemically with PEDOT/GOx which again may be coated with the copolymer of BMA and NVP. A silver plated stainless steel wire, diameter 0.152 mm, may be coated with a silverchloride layer which may also be coated with the copolymer. These three wires may be coiled in parallel around a mandrel. The formed coil then have an outer diameter of 0.87 mm. After removal of the mandrel the coil may be cut into pieces of 1 cm in length. One of the ends of the coil may be closed with a drop of UV-curable polymer. The three wires at the other end of the coil may then be connected to an electronic circuit.

Calibration curves are produced according to the procedure similar to Example 2. The measured current through the working electrode is substantially proportional to the glucose concentration.

Example 8

The coil made according to the examples 1-7 is connected to an electronic circuit component to form the biosensor. The electronic signal obtained from the sensor may be transmitted by an antenna system and received by an external device, for example mounted in a pair of glasses. This may in turn amplify the signal and transmit it to another device, for example an insulin pump.

Example 9

Two platinum wires of diameter 0.127 mm were provided to be used as the working and counter electrodes in the following steps. The platinum wires were cleaned prior to use by sequential washing in $H_2SO_4$, ultrapure water and finally in PBS.

A reference electrode was constructed as follows: an electrochemical cell was created with a silver wire of diameter 0.127 mm used as a working electrode in a saturated solution of KCl (3.4 g KCl, 10 ml MilliQ). A potential of 6V against the reference electrode was then applied for 2 times 50 s. The electrode was then kept overnight in the electrolyte solution, followed by a potentiometric measurement (zero current).

The three wires obtained as described above were coiled in parallel around a non conductive mandrel as shown in FIG. 9b.

To a stirred solution of phosphate buffered saline (PBS, 10 mL, pH 7.4) at room temperature, was added EDOT (20 □L, $2\times10^{-2}$ m), followed after 5 min by addition of polyethylene glycol (PEG, 30 mg, average Fw=6000 g/mol, $5\times10^{-4}$ m). The resulting solution was stirred for another 5 min followed by addition of glucose oxidase (7 mg, Aspergillus niger, 270 U/mg material, BBI enzymes) and stirred gently.

The parallel coiled wires and mandrel were immersed in the PBS solution containing EDOT and glucose oxidase. Cyclic voltametry (0-1.2V, 40 cycles, 0.05 V/s, against reference electrode) was used to electropolymerise EDOT on the surface of the working electrode. The parallel coiled wires were removed from the mandrel. After this, the electrodes were cut to the appropriate length.

A top coating was applied to the parallel coiled wires. The parallel coiled wires were coated in a mixture of chitosan (2 mL, 1% in MilliQ/AcOH (99:1)) and glutaraldehyde (20 uL, 25% in water) by dip-coating. The coating was allowed to dry for 2 h at room temperature and the sensor system was then suitable for use.

Example 10

A glucose calibration curve was made using the parallel coiled electrode set-up obtained by Example 9. Glucose PBS solutions from 0.00 to 1 mM with steps of 0.25 mM and from 1.0 to 5.0 mM with steps of 1 mM were prepared.

Amperometry was performed for the different solutions. One potential step of 500 mV vs Ag/AgCl was applied and the current was measured for 150 s without stirring. The average current and the standard deviation between 60 and 150 seconds was calculated and plotted against the glucose concentration.

Figure 13:
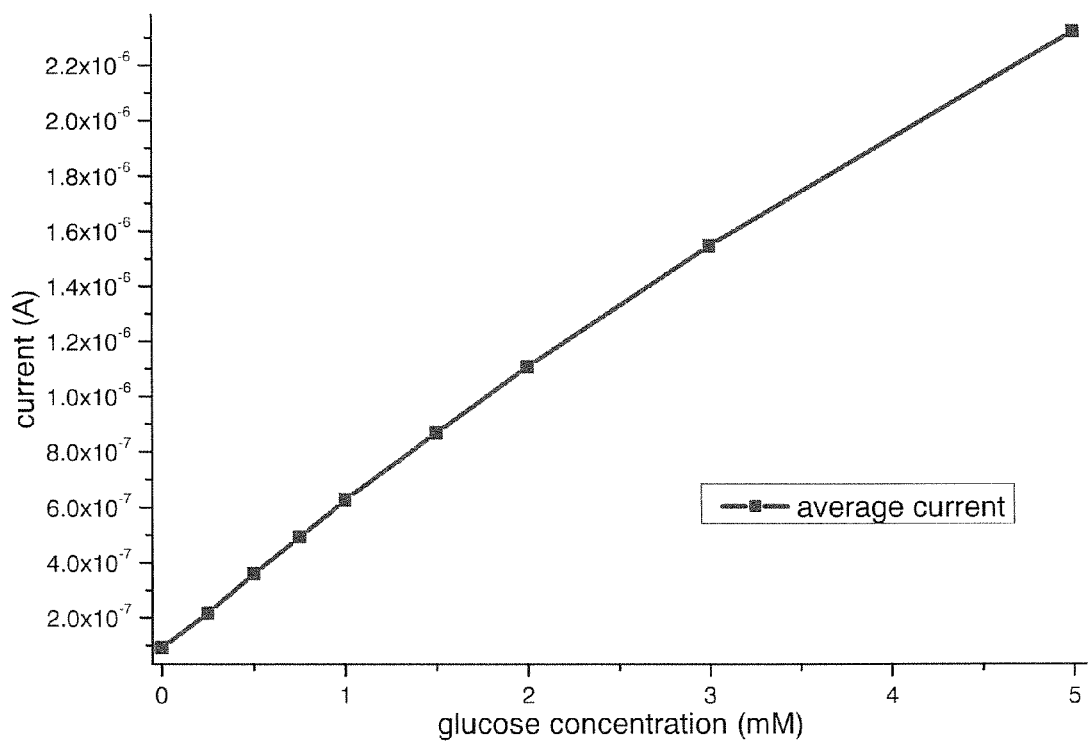

The result is shown in FIG. 13. It was observed that the current was linearly proportional to the glucose concentration in the range 0 and 5 mM.

What is claimed is:

1. A process for making a biosensor comprising a hollow coil comprising wires coiled in parallel and an electronic circuit component connected to the coil, the process comprising:
   1) providing a mandrel on which wires including at least a first wire, a second wire and a third wire are wound in parallel,
   2a) immersing the mandrel in a first buffer solution comprising a first bioreceptor and a first monomer,
   2b) arranging the wires such that the second wire is used as a working electrode, the first wire is used as a counter electrode and the third wire is used as a reference electrode of a three electrode electrochemical cell used in an electropolymerisation process,
   3) passing electric current through the second wire to form a first biocompatible coating of a first polymer polymerized from the first monomer comprising the first bioreceptor on the second wire,
   4) removing the coil from the mandrel,
   5) connecting the wires to their respective points of the electronic circuit component such that the second wire may be used, as a second working electrode, the first wire is used as a second counter electrode and the third wire is used as a second reference electrode,
   wherein the electronic circuit component is configured such that the electronic circuit component can generate an input signal for a wireless receiver based upon the activity of the bioreceptor and wirelessly send the input signal to the wireless receiver,
   wherein the first monomer is a five-membered heterocycle of formula (I)

(I)

wherein $R^1$ stands for a hetero atom,
   wherein $R^2$, $R^3$ are each, independently, selected from the group consisting of: H, an alkyl of 1 to 4 C atoms, an alkyl of 1 to 4 C atoms having a hydroxyl group, an alkyl of 1 to 4 C atoms having an alkyl group, an alkyl of 1 to 4 C atoms having an alkyl ether group, and o-alkyl, and wherein $R^2$ and $R^3$ may form a ring together with the carbon atoms to which $R^2$ and $R^3$ are connected, and
   wherein the bioreceptor is an oxidoreductase.

2. The process according to claim 1, wherein the wires include a further wire and the process further comprises the steps of:

2a') immersing the mandrel in a second buffer solution comprising a second bioreceptor and a second monomer, wherein the second bioreceptor is different from the first bioreceptor, 2b') arranging the wires such that the further wire may be used as a third working electrode, the first wire is used as a third counter electrode and the third wire is used as a third reference electrode of a second three electrode electrochemical cell used in an electropolymerisation process, 3') passing electric current through the further wire to form a second biocompatible coating of a second polymer polymerized from the second monomer comprising the second bioreceptor on the further wire and wherein step 5) comprises the step of connecting the further wire to the electronic circuit component such that the further wire may be used as a fourth working electrode.

3. The process according to claim 2, wherein the process further comprises the step of providing a biocompatible resin capping on the electric circuit component after step 5).

4. The process according to claim 3, wherein the wires further include a fourth wire coated with an insulating layer and wherein step 5) comprises the step of connecting the fourth wire to the electronic circuit component such that the fourth wire is used as an antenna.

5. The process according to claim 4, wherein the wires further include a fifth wire coated with a fifth wire insulating layer which is used as a spacer.

6. The process according to claim 5, further comprising the step of cutting the coil into a length of 5-50 mm between steps 4) and 5).

7. The process according to claim 6, further comprising the step of providing a top coating of a biocompatible material on the biosensor after step 5).

8. The process according to claim 7, wherein the sensor has a diameter of 0.1 to 3 mm.

9. The process according to claim 8, wherein the first coiled wire has a Pt surface.

10. The process according to claim 9, wherein the third coiled wire is a silver/silver chloride reference electrode, wherein the bioreceptor is an oxidoreductase of the enzyme commission groups EC 1.X.3 where X=1-17, and wherein the bioreceptor is glucose oxidase, lactate dehydrogenase, pyruvate dehydrogenase or pyruvate oxidase.

11. The process according to claim 1, wherein the process further comprises the step of providing a biocompatible resin capping on the electric circuit component after step 5).

12. The process according to claim 1, wherein the wires further include a fourth wire coated with an insulating layer and wherein step 5) comprises the step of connecting the fourth wire to the electronic circuit component such that the fourth wire is used as an antenna.

13. The process according to claim 12, wherein the wires further include a fifth wire coated with a fifth wire insulating layer which is used as a spacer.

14. The process according to claim 1, further comprising the step of cutting the coil into a length of 5-50 mm between steps 4) and 5).

15. The process according to claim 1, further comprising the step of providing a top coating of a biocompatible material on the biosensor after step 5).

16. The process according to claim 1, wherein the sensor has a diameter of 0.1 to 3 mm.

17. The process according to claim 1, wherein the first coiled wire has a Pt surface.

18. The process according to claim 1, wherein the third coiled wire is a silver/silver chloride reference electrode.

19. The process according to claim 1, wherein the bioreceptor is an oxidoreductase of the enzyme commission groups EC 1.X.3 where X=1-17.

20. The process according to claim 1, wherein the bioreceptor is glucose oxidase, lactate dehydrogenase, pyruvate dehydrogenase or pyruvate oxidase.

* * * * *